(12) United States Patent
Guttridge et al.

(10) Patent No.: US 8,426,355 B2
(45) Date of Patent: Apr. 23, 2013

(54) METHODS OF TREATING MUSCULAR WASTING DISEASES USING NF-κB ACTIVATION INHIBITORS

(75) Inventors: Denis C. Guttridge, Columbus, OH (US); Albert S. Baldwin, Chapel Hill, NC (US)

(73) Assignee: TheraLogics, Inc., Chapel Hill, NC (US)

( * ) Notice: Subject to any disclaimer, the term of this patent is extended or adjusted under 35 U.S.C. 154(b) by 1304 days.

(21) Appl. No.: 11/686,623

(22) Filed: Mar. 15, 2007

(65) Prior Publication Data

US 2007/0225315 A1    Sep. 27, 2007

Related U.S. Application Data

(60) Provisional application No. 60/782,427, filed on Mar. 15, 2006.

(51) Int. Cl.
*A61K 38/00* (2006.01)
*A61K 38/08* (2006.01)
*A61K 38/04* (2006.01)

(52) U.S. Cl.
USPC ........... 514/1.1; 514/21.6; 514/907; 530/300; 530/327

(58) Field of Classification Search .................. None
See application file for complete search history.

(56) References Cited

U.S. PATENT DOCUMENTS

| | | | |
|---|---|---|---|
| 5,137,922 A | 8/1992 | Shimamura et al. |
| 5,624,949 A | 4/1997 | Heath, Jr. et al. |
| 5,635,517 A | 6/1997 | Muller et al. |
| 5,939,302 A | 8/1999 | Goeddel et al. |
| 6,015,815 A | 1/2000 | Mollison |
| 6,030,834 A | 2/2000 | Chu et al. |
| 6,235,740 B1 | 5/2001 | Barrish et al. |
| 6,562,811 B1 | 5/2003 | Murata et al. |
| 6,824,972 B2 | 11/2004 | Kenwrick et al. |
| 6,831,057 B2 | 12/2004 | Baldwin et al. |
| 6,831,065 B2 | 12/2004 | May et al. |
| 6,831,175 B2 | 12/2004 | Li et al. |
| 6,872,715 B2 | 3/2005 | Santi et al. |
| 7,049,395 B2 * | 5/2006 | May et al. ............... 530/300 |
| 2003/0187026 A1 | 10/2003 | Li et al. |
| 2003/0236294 A1 | 12/2003 | Chen et al. |
| 2004/0097563 A1 | 5/2004 | Murata et al. |
| 2004/0186118 A1 | 9/2004 | Bryant et al. |
| 2004/0235839 A1 | 11/2004 | Hepperle et al. |
| 2005/0101594 A1 | 5/2005 | Binch et al. |

FOREIGN PATENT DOCUMENTS

| | | |
|---|---|---|
| EP | 1 535 609 A1 | 6/2005 |
| EP | 1535609 | 6/2005 |
| EP | 1 600 445 A1 | 11/2005 |
| WO | 9803502 A1 | 1/1998 |
| WO | 9901553 A1 | 1/1999 |
| WO | 0183547 | 11/2001 |
| WO | 0244153 | 6/2002 |
| WO | 03013430 A2 | 2/2003 |
| WO | 03029241 A1 | 4/2003 |
| WO | 03039545 A2 | 5/2003 |
| WO | 03076447 A1 | 9/2003 |
| WO | 03086394 A1 | 10/2003 |
| WO | 03086404 A1 | 10/2003 |
| WO | 03103654 A1 | 12/2003 |
| WO | 2004053087 A2 | 6/2004 |
| WO | 2004096131 A2 | 11/2004 |
| WO | 2005012301 A1 | 2/2005 |
| WO | 2005/062854 A2 | 7/2005 |
| WO | 2005/099687 A2 | 10/2005 |
| WO | 2006127930 | 11/2006 |

OTHER PUBLICATIONS

May et al., Semin. Cancer. Biol. 8: 63-73 (1997).
May et al., Immunol. Today 19: 80-88 (1998).
Ghosh et al., Annu. Rev. Immunol. 16: 225-260 (1998).
DiDonato et al., Nature 388: 548-554 (1997).
Takeda et al., Science 284: 313-316 (1999).
Zandi et al., Cell 91: 243-252 (1997).
Traenchner et al., Embo J. 14: 2876-2883 (1995).
DiDonato et al., Mol. Cell. Biol. 16: 1295-1304 (1996).
Yamaoke et al., Cell 93: 1231-1240 (1998).
Rothwarf et al., Nature 395: 287-300 (1998).
J. Biol. Chem. 281(5): 2551-2561 (Feb. 3, 2006).
Ghosh et al., "Missing Pieces in the NF-κB Puzzle", Cell, 109: S81-S96 (Apr. 2002).
Wykes et al., "Induction of proteasome expression in skeletal muscle is attenuated by inhibitors of NF-kappaB activation" British Journal of Cancer, 91(9):1742-1750 (Nov. 1, 2004).
Cai Dongsheng et al., "IKKbeta/NF-kappaB activation causes severe muscle wasting in mice" Cell, 119(2):285-298 (Oct. 15, 2004).
Bar-Shai Marina et al. "The role of NF-kappaB in protein breakdown in immobilization, aging, and exercise: from basic processes to promotion of health" Annals of the New York Academy of Sciences, 157:431-447 (Dec. 2005).

(Continued)

*Primary Examiner* — Christine J Saoud
*Assistant Examiner* — Jegatheesan Seharaseyon
(74) *Attorney, Agent, or Firm* — Senniger Powers LLP

(57) ABSTRACT

Methods for treating muscular wasting diseases such as Duchenne muscular dystrophy are disclosed. Specifically, the methods include administering to a subject in need of treatment for a muscular wasting disease, an NF-κB activation inhibitor capable of blocking the activation of NF-κB.

3 Claims, 6 Drawing Sheets

OTHER PUBLICATIONS

Monici et al. "Activation of nuclear factor-kappaB in inflammatory myopathies and Duchenne muscular dystrophy" Neurology, 60(6):993-997 (Mar. 25, 2003).

May et al. "Selective inhibition of NF-κB activation by a peptide that blocks the interaction of NEMO with the IkB kinase complex" Science, 289:1550-1554 (Sep. 1, 2000).

Partial Search Report from analogous application No. PCT/US2007/064057 dated Oct. 16, 2007.

Bernier, M., et al., "Binding of Manumycin A Inhibits IκB Kinase β Activity," The Journal of Biological Chemistry, Feb. 3, 2006, pp. 2551-2561, vol. 281, No. 5.

International Search Report, PCT/US2007/064057, dated Apr. 9, 2008, 11 pages.

Carlson, C. G., et al., "Chronic Treatment with Agents with Stabilize Cytosolic IkappaB-alpha Enhances Survival and Improves Resting Membrane Potential in MDX Muscle Fibers Subjected to Chronic Passive Stretch," Neurobiology of Disease, Dec. 2005, pp. 719-730, vol. 20, No. 3.

Kumar, A., at al., "Nuclear Factor-kappaB: Its Role in Health and Disease" Journal of Molecular Medicine, Jul. 2004, pp. 434-438, vol. 82, No. 7.

\* cited by examiner

Embryonic
MyHC

SEQUENCE LISTING

<160> NUMBER OF SEQ ID NOS: 20

<210> SEQ ID NO 1
<211> LENGTH: 6
<212> TYPE: PRT
<213> ORGANISM: Artificial Sequence
<220> FEATURE:
<223> OTHER INFORMATION: NBD mutants

<400> SEQUENCE: 1

Leu Asp Trp Ser Trp Leu
1               5

<210> SEQ ID NO 2
<211> LENGTH: 6
<212> TYPE: PRT
<213> ORGANISM: Artificial sequence
<220> FEATURE:
<223> OTHER INFORMATION: NBD mutants

<400> SEQUENCE: 2

Leu Asp Ala Ser Ala Leu
1               5

<210> SEQ ID NO 3
<211> LENGTH: 6
<212> TYPE: PRT
<213> ORGANISM: Artificial Sequence
<220> FEATURE:
<223> OTHER INFORMATION: NBD mutants

<400> SEQUENCE: 3

Ala Asp Trp Ser Trp Leu
1               5

<210> SEQ ID NO 4
<211> LENGTH: 6
<212> TYPE: PRT
<213> ORGANISM: Artificial Sequence
<220> FEATURE:
<223> OTHER INFORMATION: NBD mutants

<400> SEQUENCE: 4

Leu Asp Trp Ser Trp Ala
1               5

<210> SEQ ID NO 5
<211> LENGTH: 6
<212> TYPE: PRT
<213> ORGANISM: Artificial Sequence
<220> FEATURE:
<223> OTHER INFORMATION: NBD mutants

<400> SEQUENCE: 5

Ala Asp Trp Ser Trp Ala
1               5

<210> SEQ ID NO 6
<211> LENGTH: 6
<212> TYPE: PRT
<213> ORGANISM: Artificial Sequence
<220> FEATURE:
<223> OTHER INFORMATION: NDB mutants

<400> SEQUENCE: 6

Leu Ala Trp Ser Trp Leu

```
<210> SEQ ID NO 7
<211> LENGTH: 6
<212> TYPE: PRT
<213> ORGANISM: Artificial Sequence
<220> FEATURE:
<223> OTHER INFORMATION: NBD mutants

<400> SEQUENCE: 7

Leu Glu Trp Ser Trp Leu
1               5

<210> SEQ ID NO 8
<211> LENGTH: 6
<212> TYPE: PRT
<213> ORGANISM: Artificial Sequence
<220> FEATURE:
<223> OTHER INFORMATION: NBD mutant

<400> SEQUENCE: 8

Leu Asn Trp Ser Trp Leu
1               5

<210> SEQ ID NO 9
<211> LENGTH: 6
<212> TYPE: PRT
<213> ORGANISM: Artificial Sequence
<220> FEATURE:
<223> OTHER INFORMATION: NBD mutants

<400> SEQUENCE: 9

Leu Asp Ala Ser Trp Leu
1               5

<210> SEQ ID NO 10
<211> LENGTH: 6
<212> TYPE: PRT
<213> ORGANISM: Artificial Sequence
<220> FEATURE:
<223> OTHER INFORMATION: NBD mutants

<400> SEQUENCE: 10

Leu Asp Phe Ser Trp Leu
1               5

<210> SEQ ID NO 11
<211> LENGTH: 6
<212> TYPE: PRT
<213> ORGANISM: Artificial Sequence
<220> FEATURE:
<223> OTHER INFORMATION: NBD mutants

<400> SEQUENCE: 11

Leu Asp Tyr Ser Trp Leu
1               5

<210> SEQ ID NO 12
<211> LENGTH: 6
<212> TYPE: PRT
<213> ORGANISM: Artificial Sequence
<220> FEATURE:
<223> OTHER INFORMATION: NBD mutants

<400> SEQUENCE: 12

Leu Asp Trp Ser Ala Leu
1               5
```

```
<210> SEQ ID NO 13
<211> LENGTH: 6
<212> TYPE: PRT
<213> ORGANISM: Artificial Sequence
<220> FEATURE:
<223> OTHER INFORMATION: NBD mutants

<400> SEQUENCE: 13

Leu Asp Trp Ser Phe Leu
1               5

<210> SEQ ID NO 14
<211> LENGTH: 6
<212> TYPE: PRT
<213> ORGANISM: Artificial Sequence
<220> FEATURE:
<223> OTHER INFORMATION: NBD mutants

<400> SEQUENCE: 14

Leu Asp Trp Ser Trp Leu
1               5

<210> SEQ ID NO 15
<211> LENGTH: 6
<212> TYPE: PRT
<213> ORGANISM: Artificial Sequence
<220> FEATURE:
<223> OTHER INFORMATION: NBD mutants

<400> SEQUENCE: 15

Leu Asp Trp Ala Trp Leu
1               5

<210> SEQ ID NO 16
<211> LENGTH: 6
<212> TYPE: PRT
<213> ORGANISM: Artificial Sequence
<220> FEATURE:
<223> OTHER INFORMATION: NBD mutants

<400> SEQUENCE: 16

Leu Asp Trp Glu Trp Leu
1               5

<210> SEQ ID NO 17
<211> LENGTH: 28
<212> TYPE: PRT
<213> ORGANISM: Artificial Sequence
<220> FEATURE:
<223> OTHER INFORMATION: NBD peptides

<400> SEQUENCE: 17

Asp Arg Gln Ile Lys Ile Trp Phe Gln Asn Arg Arg Met Lys Trp Lys
1               5                   10                  15

Lys Thr Ala Leu Asp Trp Ser Trp Leu Gln Thr Glu
            20                  25

<210> SEQ ID NO 18
<211> LENGTH: 28
<212> TYPE: PRT
<213> ORGANISM: Artificial Sequence
<220> FEATURE:
<223> OTHER INFORMATION: NBD peptides

<400> SEQUENCE: 18

Asp Arg Gln Ile Lys Ile Trp Phe Gln Asn Arg Arg Met Lys Trp Lys
1               5                   10                  15
```

```
Lys Thr Ala Leu Asp Ala Ser Ala Leu Gln Thr Glu
            20                  25

<210> SEQ ID NO 19
<211> LENGTH: 11
<212> TYPE: PRT
<213> ORGANISM: Artificial Sequence
<220> FEATURE:
<223> OTHER INFORMATION: NBD mutants

<400> SEQUENCE: 19

Thr Ala Leu Asp Trp Ser Trp Leu Gln Thr Glu
1               5                   10

<210> SEQ ID NO 20
<211> LENGTH: 11
<212> TYPE: PRT
<213> ORGANISM: Artificial Sequence
<220> FEATURE:
<223> OTHER INFORMATION: NBD mutants

<400> SEQUENCE: 20

Thr Ala Leu Asp Ala Ser Ala Leu Gln Thr Glu
1               5                   10
```

METHODS OF TREATING MUSCULAR WASTING DISEASES USING NF-κB ACTIVATION INHIBITORS

REFERENCE TO RELATED APPLICATION

This application claims the benefit of U.S. Provisional Application Ser. No. 60/782,427 which was filed Mar. 15, 2006. The entire content of the provisional application is incorporated herein by reference.

BACKGROUND OF THE DISCLOSURE

The present invention generally relates to treating muscular wasting diseases by inhibiting the NF-κB pathway.

Muscular wasting diseases, such as muscular dystrophies, are a group of degenerative diseases that culminate in progressive skeletal muscle wasting leading to muscle weakness, wheelchair dependence, and in some cases death. Of the muscular dystrophies, Duchenne muscular dystrophy is the most severe and most widely recognized. Duchenne muscular dystrophy occurs in one in 3500 male births per year and is the most frequent of all lethal X-linked recessive diseases. Duchenne muscular dystrophy symptoms typically appear in boys by the ages of 3 to 5 years old. By their teenage years these affected boys are wheelchair bound, and by their second or third decade of life, they usually succumb to the disease due to diaphragm and/or cardiac muscle dysfunction.

Another muscular wasting disease, which shows similar symptoms, although less severe, as Duchenne muscular dystrophy, is Becker muscular dystrophy. Even though the defective dystrophin gene causing both Duchenne muscular dystrophy and Becker muscular dystrophy has been known for over 20 years, a cure is still lacking.

Also included in the class of muscular dystrophies, yet not as well-known as Duchenne muscular dystrophy or Becker muscular dystrophy, is Limb Girdle muscular dystrophy. Specifically, for many types of Limb Girdle muscular dystrophy, the defective gene causing the disease is not yet known.

SUMMARY OF THE DISCLOSURE

Among the various aspects of the present invention is a method for inactivating the NF-κB pathway to treat a muscular wasting disease. The method comprises administering to the subject an NF-κB activation inhibitor or prodrug thereof for the purpose of inhibiting the muscular wasting disease. Muscle wasting diseases which may be treated in this manner include muscular dystrophies such as Duchenne muscular dystrophy, Becker muscular dystrophy, and Limb Girdle muscular dystrophy. Other muscular wasting diseases that can also be treated using the method described herein include polymyositis, dermatomyositis, cancer cachexia, AIDS cachexia, cardiac cachexia, and muscle atrophy.

Other aspects of the disclosure will be in part apparent and in part pointed out hereinafter.

DETAILED DESCRIPTION OF THE PREFERRED EMBODIMENT

Figure 1:
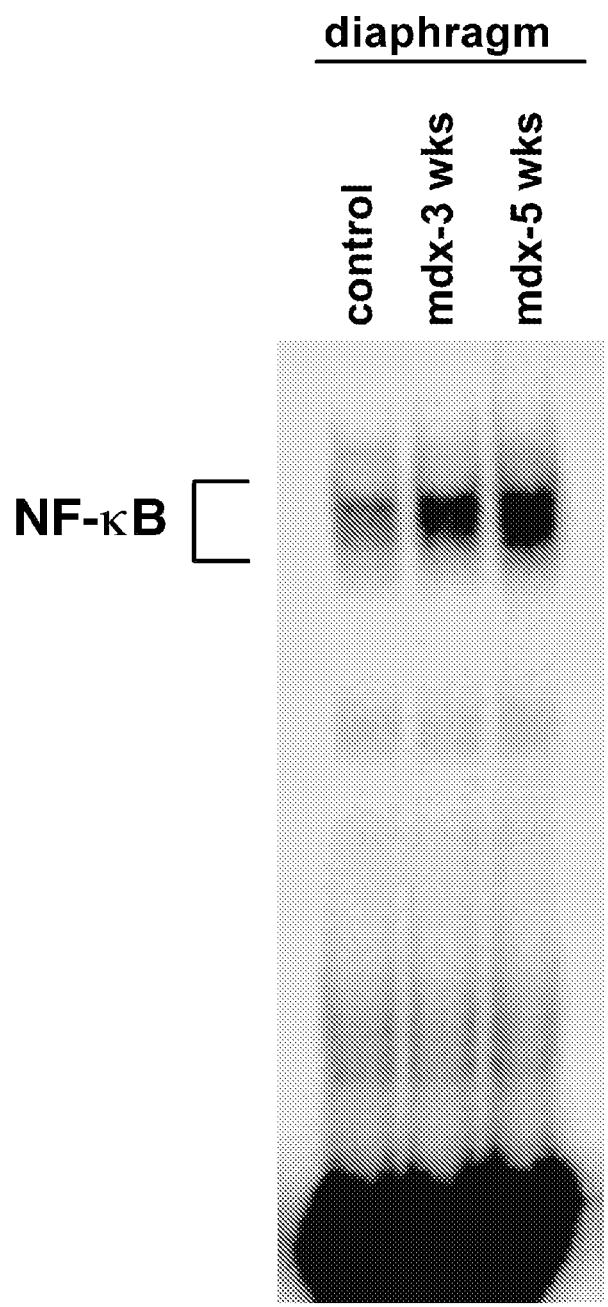
FIG. 1 depicts the NF-κB activity in the diaphragm muscles of control and mdx-/- mice as evaluated using EMSA in Example 1.

In accordance with the present invention, it has been discovered that NF-κB is chronically activated in skeletal muscle degeneration associated with muscular wasting diseases such as muscular dystrophies. Thus, the present invention is directed to methods of treating these muscular wasting diseases by inactivating the NF-κB pathway, thereby blocking the extracellular signals responsible for the induction of genes causing muscle deterioration.

In one embodiment, the method comprises administering to the subject an NF-κB activation inhibitor or prodrug thereof for the purpose of inhibiting the disease. The subject may be any human or animal subject who is affected by a muscular wasting disease or who is at risk for developing a muscular wasting disease. Thus, an animal subject, for example, may be a domestic livestock species, a laboratory animal species, a zoo animal or a companion animal. In one preferred embodiment, the subject is a mammal. In one particularly preferred embodiment, the mammal is a human.

Muscular Wasting Diseases

Typically, the methods of the present disclosure can be used for the treatment of a number of muscular wasting diseases. The muscular wasting diseases can generally be divided into three categories: (1) muscular dystrophies; (2) inflammatory myopathies; and (3) muscle atrophies. Muscular dystrophies for treatment with the method of the present disclosure include, for example, Duchenne muscular dystrophy, Becker muscular dystrophy, and Limb Girdle muscular dystrophy. As noted above, muscular dystrophies are hereditary, progressive, and each type causes a characteristic, selective pattern of muscle weakness.

Duchenne muscular dystrophy and Becker muscular dystrophy are similar in that these dystrophies share similar patterns of muscle weakness and disability and are inherited in the same way. Typically, subjects in need of treatment for Duchenne or Becker muscular dystrophies have trouble walking and eventually become wheelchair dependent. Generally, an arbitrary means of distinguishing between Duchenne muscular dystrophy and Becker muscular dystrophy depends on whether the affected subject can still walk at 16 years of age. Subjects with Duchenne muscular dystrophy are generally wheelchair bound by their teenage years. More specifically, a muscle biopsy of a subject affected with Duchenne muscular dystrophy will show more disabling change as compared to a subject affected with Becker muscular dystrophy.

Duchenne muscular dystrophy and Becker muscular dystrophy are due to defects or mutations of the same gene, which is directed to enabling muscle fibers to make dystrophin. The dystrophin gene encodes a large 427 kDa protein that functions in linking the extracellular matrix to the muscle fiber cytoskeleton. The amino terminus on dystrophin binds to filamentous actin in contact with the contractile apparatus of skeletal muscle, while a cysteine-rich domain near the carboxyl terminus binds to dystroglycan proteins localized to the fiber membrane in connection with other membrane proteins that constitute the dystrophin glycoprotein complex (DGC). The absence of dystrophin expression causes a concomitant decrease in DGC members. It is now believed that loss of dystropin and the resulting DGC complex compromises the integrity of skeletal muscle membranes, which undergo damage after repeated cycles of contractile activity. Membrane damage is further thought to cause creatine kinase release, stimulate the influx of calcium, and induce the recruitment of immune T cells, macrophages, and mast cells, culminating in muscle fiber necrosis. The regenerative capacity of these cells become exhausted in Duchenne muscular dystrophy patients, thus giving way to accumulated fibrosis and fatty deposits that exacerbates the muscle wasting process.

Limb Girdle muscular dystrophies include at least ten different inherited disorders that can further be classified into two categories, autosomal-dominant (LGMD 1) and autosomal-recessive (LGMD 2) syndromes. The symptoms of most Limb Girdle muscular dystrophies typically begin with pelvic muscle weakness starting in childhood to young adulthood. Later, there is an onset of shoulder weakness with progression to significant loss of mobility or wheelchair dependence over the next 20-30 years.

The defective gene causing most autosomal-dominant type Limb Girdle muscular dystrophies has not yet been discovered, but the diseases have been linked to mutations in various chromosomes. For example, LGMD 1A type dystrophy has been linked to chromosome 5. Additionally, LGMD 1B type dystrophy has been linked to chromosome 1. Other chromosomes that have been linked to the autosomal-dominant type Limb Girdle muscular dystrophies include chromosomes 3 and 7. Several of the autosomal-recessive type Limb Girdle muscular dystrophies are due to mutations in the dystrophin-associated glycoproteins (i.e., sarcoglycans).

Another embodiment encompasses using the method of the present disclosure to treat an inflammatory myopathy. Inflammatory myopathies are diseases or abnormal conditions of the striated skeletal muscles. The cause of most inflammatory myopathies is unknown. Typically, inflammatory myopathies are believed to result from an autoimmune reaction, whereby the body's own immune system attacks the muscle cells. Examples of inflammatory myopathies for treatment can include polymyositis and dermatomyositis.

Symptoms of polymyositis include muscle inflammation and muscle tenderness. The onset of symptoms may be acute, but the condition usually progresses slowly and, if left untreated, may compromise the subject's ability to walk.

Subjects in need of treatment for dermatomyositis have similar symptoms as with polymyositis, but additionally show signs of a distinctive skin rash. Specifically, a violet-colored or dusky red rash breaks out over the subject's face, eyelids, and areas around their nails, knuckles, elbows, knees, chest, and back. Dermatomyositis typically occurs in adult subjects in their late 40s to early 60s or in children between the ages of 5 and 15.

In yet another embodiment, the method of the present disclosure can be utilized to treat muscle atrophy. Muscle atrophy can be the result of a disorder or condition such as cancer cachexia, AIDS cachexia, or cardiac cachexia. Cachexia is generally associated with the massive loss (up to 30% of total body weight) of both adipose tissue and skeletal muscle mass that may occur as a side effect of many diseases such as cancer, AIDS, and chronic heart failure. The loss of adipose tissue and skeletal muscle mass can lead to anorexia, early satiety, fatigue, generalized muscle weakness, decreased muscle function, and progressive muscle wasting.

Recently, major advances have been made in the identification of catabolic factors that act to destroy host tissues during the cachectic process. Although anorexia is frequently present, depression of food intake alone seems not to be responsible for the wasting of body tissue, as nutritional supplementation or pharmacological manipulation of appetite is unable to reverse the catabolic process, particularly with respect to skeletal muscle wasting. It now appears that the oversecretion of inflammatory cytokines, specifically tumor necrosis factor-alpha (TNF-$\alpha$), is one of the most likely causes of cachexia. Specifically, TNF-$\alpha$ can mimic most of the abnormalities that occur in cachexia such as weight loss, anorexia, increased thermogenesis, changes in lipid metabolism, insulin resistance, and muscle wasting.

Furthermore, muscle atrophy can be induced by the loss of innervation or damage to innervation of the muscle tissue. Specifically, diseases such as chronic neuropathy and motor neuron disease can cause damage to innervation. Moreover, many times a physical injury to the nerve can lead to damage to the innervation of the muscle tissue.

Alternatively, muscle atrophy can be the result of environmental conditions such as during spaceflight or as a result of aging or extended bed rest. Under these environmental conditions, the muscles do not bear the usual weight load, resulting in muscle atrophy from disuse. Specifically, during muscle disuse, intracellular processes are activated to induce proteolysis mainly through the ATP dependent ubiquitin proteasome pathway, which regulates the NF-$\kappa$B pathway.

Diagnosis of Muscular Wasting Diseases

Methods for identifying a subject in need of treatment for a muscular wasting disease are generally known. For example, a subject in need of treatment for a muscular wasting disease will often generate less electrical activity during muscle contraction as compared to a healthy subject and this should be detected by electromyography. Alternative methods for diagnosis include, for example, blood tests and muscle biopsies. Suitably, blood tests can be run to determine the levels of various constituents of muscle and muscle fibers. For example, many muscular wasting diseases can be diagnosed by conducting a blood test to measure the level of creatinine in the blood. Creatinine is a breakdown product of creatine, which is an important constituent of muscle. In another embodiment, a blood test for determining the amount of creatine phosphokinase (CPK), which is an enzyme found predominantly in the heart, brain, and skeletal muscle, can be conducted to diagnose a subject in need for treatment of a muscular wasting disease. Specifically, when the total CPK level is substantially elevated, it usually indicates injury or stress to one or more of the heart, brain, and skeletal muscle. In yet another embodiment, subjects affected by either Duchenne muscular dystrophy or Becker muscular dystrophy, can be diagnosed by measuring the level of dystrophin. Typically, in subjects with either Duchenne muscular dystrophy or Becker muscular dystrophy, the level of dystrophin is deficient; but, in a subject with Duchenne muscular dystrophy, the level is more severely deficient. Specifically, many Duchenne muscular dystrophy patients are null for dystrophin expression resulting from an out of frame deletion.

Muscle biopsies are also suitable means of diagnosing a subject in need of treatment for a muscular wasting disease. Generally, during a muscle biopsy, a small piece of muscle tissue is removed surgically for laboratory analysis. The analysis can then reveal abnormalities in the muscle, such as inflammation, damage, or infection.

In yet another embodiment, the subject can be diagnosed for a muscular wasting disease using magnetic resonance imagining (MRI). During an MRI, cross-sectional images of muscle are generated by a magnetic field and radio waves. Similar to the muscle biopsy analysis above, the image generated by an MRI can reveal abnormalities in the muscle, such as inflammation, damage, or infection.

NF-κB Activation Inhibitors

NF-κB is known to mediate extracellular signals responsible for the induction of genes involved in pro-inflammatory responses. NF-κB is located in the cytoplasm of most non-stimulated cells by a non-covalent interaction with one of several proteins known as IκBs (May & Ghosh, (1997) Semin. Cancer. Biol. 8, 63-73; May & Ghosh, (1998) Immunol. Today 19, 80-88; Ghosh et al., (1998) Annu. Rev. Immunol. 16, 225-260). Cellular stimuli associated with pro-inflammatory responses such as tumor necrosis factor-alpha (TNF-α) activate kinases, which in turn activate NF-κB by phosphorylating IκBS. The kinases that phosphorylate IκBs are called IκB kinases (IKKs).

Phosphorylation targets IκBs for subsequent ubiquitination and degradation. This degradation of IκBs reveals the nuclear localization signal on NF-κB, allowing nuclear accumulation of activation, which leads to binding of DNA and control of specific gene expression. Phosphorylation of IκB is therefore an important step in the regulation of NF-κB downstream of many stimuli, although other mechanisms can lead to the activation of functional NF-κB.

The identification and characterization of kinases that phosphorylate IκBs has led to a better understanding of signaling pathways involving NF-κB activation. Several different subtypes of IKK have been identified thus far. IKKα was initially identified as an IκB kinase induced by TNFα stimulation in HeLa cells (DiDonato et al., (1997) Nature 388, 548-554). Another IκB kinase homologous to IKKα was identified, termed IKKβ, and determined to be the major IκB kinase induced following TNFα stimulation (Takeda et al., (1999) Science 284, 313-316; U.S. Pat. No. 6,030,834, issued to Pots et al. (2000); U.S. Pat. No. 5,939,302, issued to Woronicz et al. (1999)). IKKα and IKKβ have an overall homology of 52% and a 65% homology in the kinase domain (Zandi et al., (1997) Cell 91, 243-252).

IκB protein kinases (IKKs) phosphorylate IκBs at specific serine residues. Specifically, they phosphorylate serines 32 and 36 of IκBα (Traenckner et al., (1995) EMBO J. 14, 2876-2883; DiDonato et al., (1996) Mol. Cell. Biol. 16, 1295-1304). Phosphorylation of both sites is required to efficiently target IκBα for degradation. Furthermore, activation of IκKα and IκKβ is usually in response to NF-κB activating agents including phorbol 12-myristate 13-acetate (PMA), lipopolysaccharide (LPS), interleukin-1 (IL-1), tumor necrosis factor-alpha (TNFα), reactive oxygen species, and DNA damaging agents. Mutant IKKα and IKKβ, which are catalytically inactive, can be used to block NF-κB stimulation. IκB kinases are therefore essential in the regulation of NF-κB activation processes downstream of inflammatory stimuli. In other pathways, IκB kinases may not be important.

IKKα and IKKβ have distinct structural motifs including an amino terminal serine-threonine kinase domain separated from a carboxyl proximal helix-loop-helix domain by a leucine zipper domain. These structural characteristics are unlike other kinases, and the non-catalytic domains are thought to be involved in protein-protein interactions. As such, proteins which bind to IKKs should be capable of regulating the activity of NF-κB and potentially regulating downstream events such as induction of NF-κB. For instance, NEMO (NF-κB Essential Modulator) is a protein which has been identified to bind to IKKs and facilitate kinase activity (Yamaoke et al., (1998) Cell 93, 1231-1240; Rothwarf et al., (1998) Nature 395, 287-300).

As shown in the Examples below, chronic NF-κB activation is associated with muscular wasting diseases such as Duchenne muscular dystrophy. Specifically, as shown an Example 2 below, muscle wasting was largely prevented in subjects that were heterozygous for the p65/RelA NF-κB subunit. Additionally, in Example 3, an injection of an NF-κB activation inhibitor peptide was found to inhibit the dystrophic phenotype in affected mice subjects. Without being bound by a particular theory, it appears that chronic activation of NF-κB is required for the muscle wasting symptoms of Duchenne muscular dystrophy. As such, a drug-based therapy targeting NF-κB can be an effective strategy to treat Duchenne muscular dystrophy, as well as other forms of muscular wasting diseases.

In general, muscular wasting diseases may be treated in accordance with the present disclosure with a direct or indirect inhibitor of NF-κB. Indirect inhibitors of NF-κB include, for example, inhibitors of IκB kinases (IKKs) such as IKKα inhibitors and IKKβ inhibitors, and inhibitors functioning directly upstream from IKKs in the signaling pathway such as inhibitors of phosphoinositide dependent kinase (PDK) and inhibitors of Akt (also referred to as PKB). A number of indirect inhibitors are identified herein.

As noted above, one suitable approach for blocking the NF-κB pathway is by binding to one of the IκB protein kinases (IKKs). By binding the IKKs, phosphorylation of IκBs is blocked and NF-κB cannot be activated. In one embodiment, direct inhibiting compounds of IKK catalytic activity can be administered for the purpose of blocking the NF-κB pathway and inhibiting a muscular wasting disease. Specifically, inhibitors of IKKα or their enantiomers, analogs, prodrugs, active metabolites, salts, and/or hydrates thereof can be administered to the subject for the purpose of inhibiting a muscular wasting disease.

In one embodiment, the IKKα inhibitor is 2H-1-Benzopyran-2-one, 5,7-dihydroxy-8-(3-methyl-2-butenyl)-6-(2-methyl-1-oxopropyl)-4-phenyl, better known as Mesuol. This inhibitor has the formula:

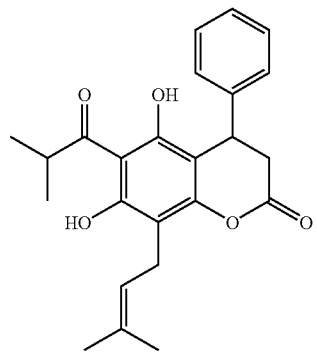 [SMILES: CC(C)=CCc1c(O)c(C(=O)C(C)C)c(O)c2c1OC(=O)CC2c1ccccc1]

In another embodiment, the IKKα inhibitor is 2-methyl-2-(2-methylpropenyl)-2,3-dihydronaphthoquinone[2,3-b]furan-4,9-dione, better known as NFD-37, and having the formula:

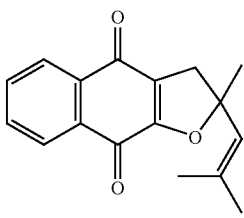 [SMILES: CC(C)=CC1(C)CC2=C(O1)C(=O)c1ccccc1C2=O]

In another embodiment, inhibitors of IKKβ or prodrugs thereof are administered to treat the muscular wasting disease.

In one embodiment, the IKKβ inhibitor is L-dehydroascorbic acid, having the formula:

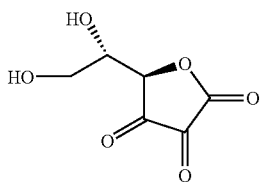 [SMILES: O=C1O[C@H]([C@@H](O)CO)C(=O)C1=O]

In another embodiment, the IKKβ inhibitor is a carboline derivative as described in PCT Application No. WO 03/039545, which is hereby incorporated by reference in its entirety.

Another group of IKKβ inhibitors includes 4-aryl pyridine derivatives described more fully in U.S. Application No. 2004/0097563, which is hereby incorporated by reference in its entirety.

Yet another IKKβ inhibitor group for use in the method of the present disclosure includes the amino-substituted tetracyclic compounds described in U.S. Pat. No. 6,235,740, which is hereby incorporated by reference in its entirety.

In another embodiment, the IKKβ inhibitor is (−)-7-[2-cyclopropylmethoxy)-6-hydroxy-phenyl]-5-[(3S)-3-peperidinyl]-1,4-dihydro-2H-pyrido[2,3-d][1,3]oxazin-2-one having the formula:

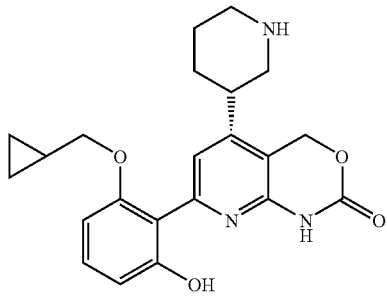

and salts thereof as described in PCT Application No. WO 03/076447, which is hereby incorporated by reference in its entirety.

Another IKKβ inhibitor group includes the heteroaromatic carboxamide derivatives described more fully in PCT Application No. WO 2001/058890, which is hereby incorporated by reference in its entirety.

In another embodiment, examples of IKKβ inhibitors are 2-ureidothiophene compounds and their derivatives described in PCT Application Nos. WO 03/029241 and WO 2004/053087, which are both hereby incorporated by reference in their entireties.

In yet another embodiment, the IKKβ inhibitors can be the diarylamide compounds as more fully described in PCT Application Nos. WO 02/049632 and WO 03/103654, which are both hereby incorporated by reference in their entireties.

Another group of IKKβ inhibitors includes pyridine derivatives as described in U.S. Pat. No. 6,562,811, which is hereby incorporated by reference in its entirety.

In another embodiment, examples of IKKβ inhibitors are beta-carboline compounds described more fully in U.S. Application No. 2004/235839, which is hereby incorporated by reference in its entirety.

Exemplary IKKβ inhibitors as generally described above are depicted in Table 1 below:

TABLE 1

Examples of IKKβ Inhibitors As Embodiments

| Compound name | Structural Formula |
|---|---|
| PS-1145 | |
| | |
| BMS-345541 | |
| | |
| | |

TABLE 1-continued

Examples of IKKβ Inhibitors As Embodiments

| Compound name | Structural Formula |
|---|---|
| TPCA-1 | |
| IMD-0354 | |
| ACHP | |
| ML-120B | |

In yet another embodiment, inhibitors of the association formed between IKKγ and IKKβ in the NF-κB pathway or prodrugs thereof are administered to treat the muscular wasting disease. For example, compounds comprising an NF-κB Essential Modulator (NEMO) binding domain or other small molecule mimetics thereof can be administered to inhibit the muscular wasting disease. As noted above, it has been found that NEMO binding domain-containing compounds can bind to IKKs and facilitate kinase activity. In one embodiment, the NEMO binding domain-containing compounds can include, for example: (a) polypeptides having an amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, and SEQ ID NO: 18; (b) a peptide fragment of at least three amino acids of the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, and SEQ ID NO: 18; (c) peptides which include a conservative amino acid substitution of the amino acid sequences of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, and SEQ ID NO: 18; and (d) naturally occurring amino acid sequence variants of the amino acid sequences of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, and SEQ ID NO: 18. These polypeptides are described more fully in U.S. Pat. No. 6,831,065, which is hereby incorporated by reference in its entirety. In one embodiment, the compound comprising the NEMO binding domain is SEQ ID NO: 19.

In another embodiment, the NEMO binding domain-containing compound is *Streptomyces parvulus* metabolite, described in J. Biol. Chem. (Feb. 3, 2006), Vol. 281, Issue 5, pp. 2551-2561.

Another particularly preferred NEMO binding domain-containing compound is Manumycin A or its enantiomers, analogs, prodrugs, active metabolites, salts, and/or hydrates thereof having the formula:

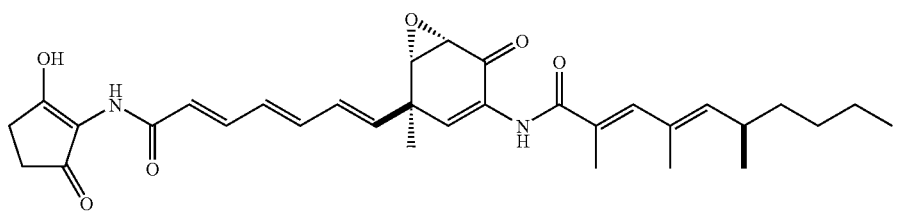 [SMILES: CCCC[C@@H](C)/C=C(C)/C=C(\C)C(=O)NC1=C[C@@](C)(/C=C/C=C/C=C/C(=O)NC2=C(O)CCC2=O)[C@@H]2O[C@@H]2C1=O]

Additionally, other compounds or their enantiomers, analogs, prodrugs, active metabolites, salts, and/or hydrates thereof that inhibit upstream kinases, regulatory molecules, or receptors, which control downstream IKK activity, can be used in the method of treating muscular wasting diseases. Specifically, in one embodiment, inhibitors of phosphoinositide dependent kinase (PDK) can be used in the method of the present disclosure. PDK is a regulator of the Akt pathway described below. More specifically, the Akt pathway can target NF-κB activation.

In one embodiment, the PDK inhibitors are the pyrazols described in U.S. Patent Application No. 2003/236294, which is hereby incorporated by reference in its entirety.

Another group of PDK inhibitors can include the pyrimadine derivatives described in U.S. Application No. 2004/186118, which is hereby incorporated by reference in its entirety.

Yet another group of PDK inhibitors are the pyrrolo[3,4-c]pyrazoles described in U.S. Application No. 2005/101594, which is incorporated by reference in its entirety.

Exemplary inhibitors of PDK as generally described above are depicted in Table 2 below:

TABLE 2

Examples of PDK Inhibitors As Embodiments

| Compound name | Structural Formula |
|---|---|
| UCN-01 | (structure shown) |
| OSU-02067 | (structure shown) |
| OSU-03012 or OSU-03013 | (structure shown) wherein R is selected from the group consisting of $H_2NCH_2CO$ and $H_2NCN$ |
| | (structure shown) wherein X is a halogen and R is selected from the group consisting of 2-thienyl and $H_2NCOC(CH_3)_2CO$ |

TABLE 2-continued

Examples of PDK Inhibitors As Embodiments

Compound name    Structural Formula

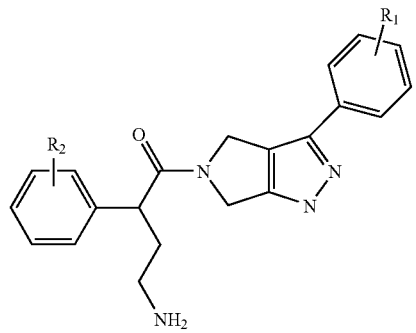

wherein $R_1$ and $R_2$ are independently selected from the group
consisting of a halogen and $CO_2H$

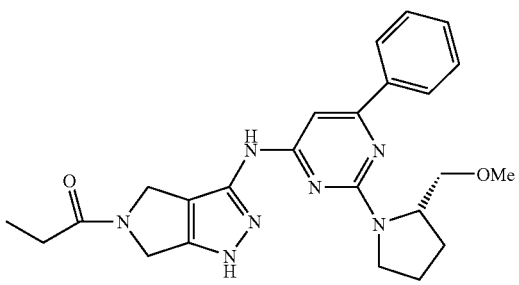

In yet another embodiment, inhibitors of MAP3K can be used in the method of the present disclosure for treating muscular wasting diseases. Specifically, MAP3K inhibitors include inhibitors of MEKK1 and NIK kinases, which can both target NF-κB activation. An example of MAP3K inhibitors include the pyrazoloisoquinoline derivatives, which target the NIK kinases, as described in PCT Application No. WO 2005/012301, which is incorporated by reference in its entirety. One particularly preferred example has the formula:

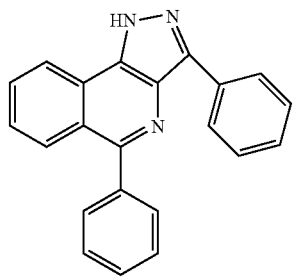 [SMILES: c1ccc(-c2nc3c(-c4ccccc4)n[nH]c3c3ccccc23)cc1]

Additionally, inhibitors of Akt (also referred to as PKB) can be used in the methods of the present disclosure. Specifically, the Akt pathway can target NF-κB activation.

In one embodiment, epigallacatechin gallate as described in U.S. Pat. No. 5,137,922, which is incorporated by reference to the extent it is consistent herewith, can be used as an inhibitor of Akt. Epigallacatechin gallate has the structural formula:

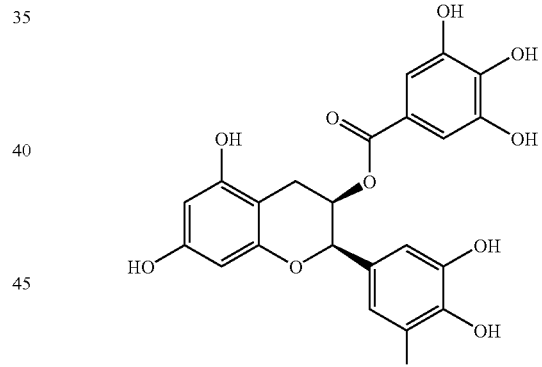

In yet another embodiment, the Akt inhibitors can be fused quinoxaline derivatives as described in PCT Application No. WO 03/086404, which is hereby incorporated by reference in its entirety.

In another embodiment, Akt inhibitors comprising a 2,3-diphenylquinoxaline moiety as described in PCT Application No. WO 03/086394, which is incorporated herein by reference in its entirety, are administered in the methods of treating muscular wasting diseases described herein.

In yet another embodiment, the pyridine derivatives described in PCT Application No. WO 2004/096131, which is incorporated by reference in its entirety, can be used as the Akt inhibitors.

Another group of Akt inhibitors includes the pyridine derivatives described in U.S. Application No. 2003/0187026, which is incorporated herein by reference in its entirety.

In another embodiment, the pyridine derivatives described in U.S. Pat. No. 6,831,175, which is incorporated herein by reference in its entirety, are used as Akt inhibitors.

Exemplary Akt inhibitors as generally described above are depicted in Table 3 below:

TABLE 3

Examples of Akt Inhibitors As Embodiments

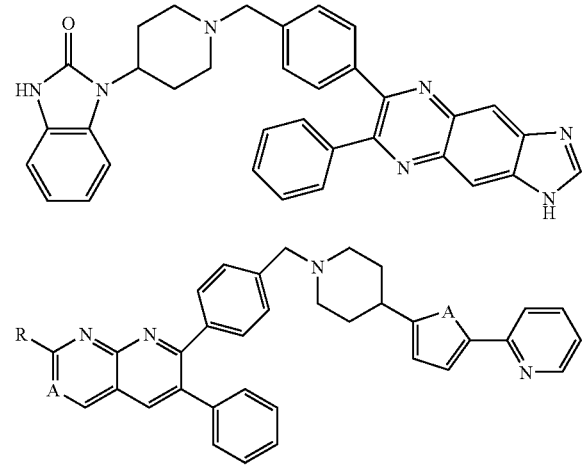

wherein R is selected from the group consisting of H and SMe and A is selected from the group consisting of CH and N

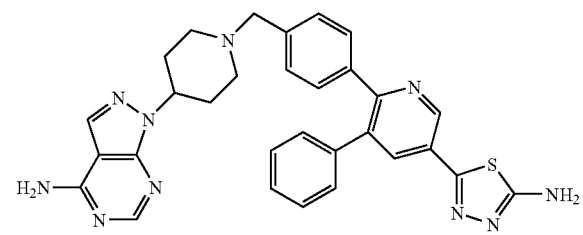 [SMILES: Nc1nnc(-c2cnc(-c3ccc(CN4CCC(n5ncc6c(N)ncnc65)CC4)cc3)c(-c3ccccc3)c2)s1]

TABLE 3-continued

Examples of Akt Inhibitors As Embodiments

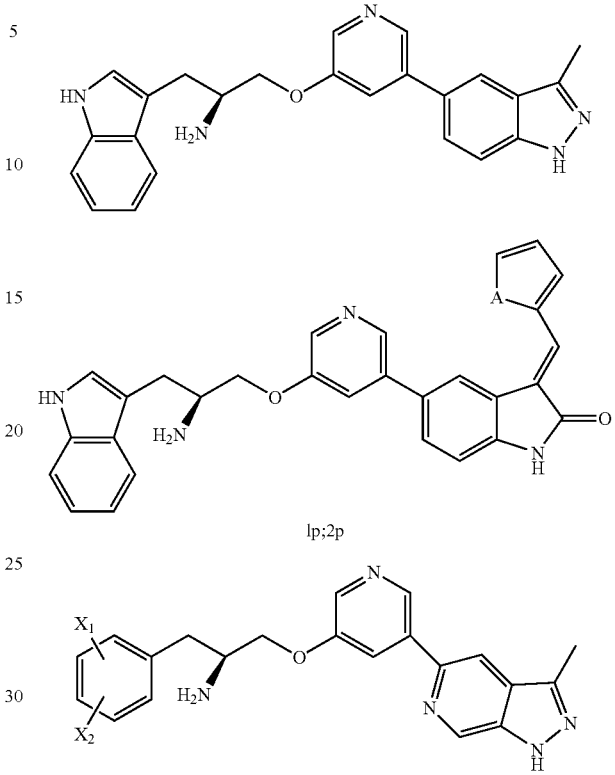

lp;2p wherein $X_1$ and $X_2$ are independently selected from the group consisting of H, a halogen, and $CF_3$ In still yet another embodiment of the present disclosure, inhibitors of Protein Kinase C (PKC) can be used in the method of the present disclosure for inhibiting muscular-wasting diseases. Examples of PKC inhibitors include those listed in Table 4 below, as well as their enantiomers, analogs, prodrugs, active metabolites, salts and hydrates thereof:

TABLE 4

Examples of PKC Inhibitors As Embodiments

Common name    Structural Formula

UNC-01

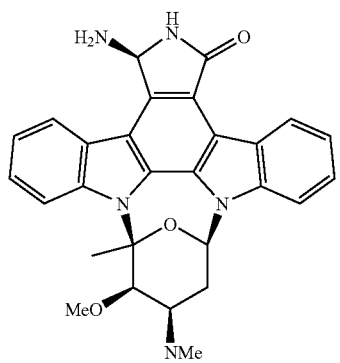

TABLE 4-continued
Examples of PKC Inhibitors As Embodiments
| Common name | Structural Formula |
|---|---|
| Hypericin | 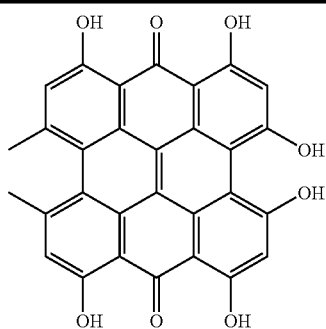 |
| Edetic acid | 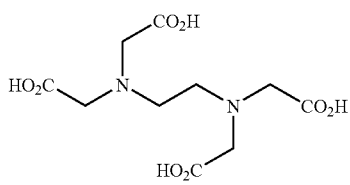 [SMILES: O=C(O)CN(CCN(CC(=O)O)CC(=O)O)CC(=O)O] |
| Safingol | 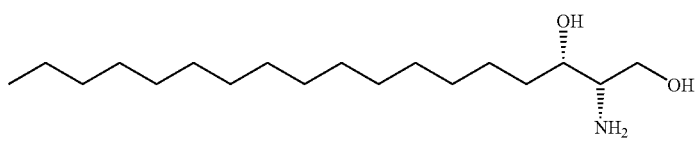 |
| Ruboxistaurin | 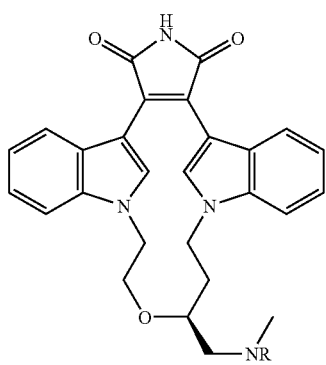<br>wherein R is hydrogen |
| LY-338522 | As described in PCT Application U.S. Pat. No. 5,624,949, which is incorporated herein by reference to the extent it is consistent herewith. |
| Enzastaurin | 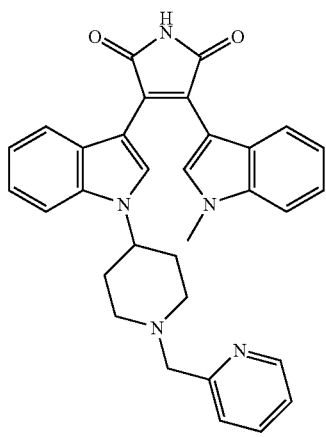 [SMILES: Cn1cc(C2=C(c3cn(C4CCN(Cc5ccccn5)CC4)c4ccccc34)C(=O)NC2=O)c2ccccc21] |

TABLE 4-continued
Examples of PKC Inhibitors As Embodiments
| Common name | Structural Formula |
|---|---|
| Novobiocin sodium | 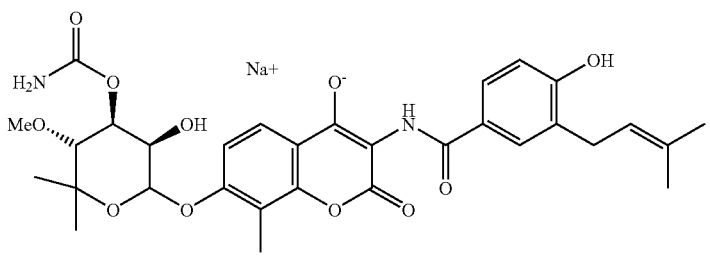 |
| NSC-330507 | 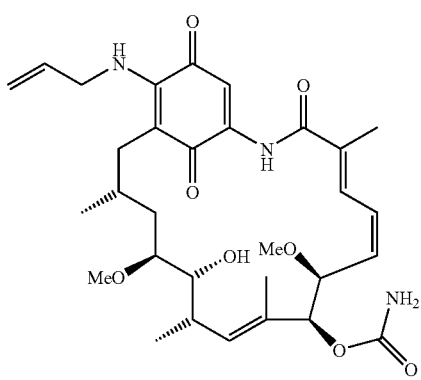 |
| IPI-504 | As described in PCT Application WO 2003/013430 and U.S. Pat. No. 6,872,715, which are both incorporated herein by reference to the extent they are consistent herewith. |
| 17-DMAG | 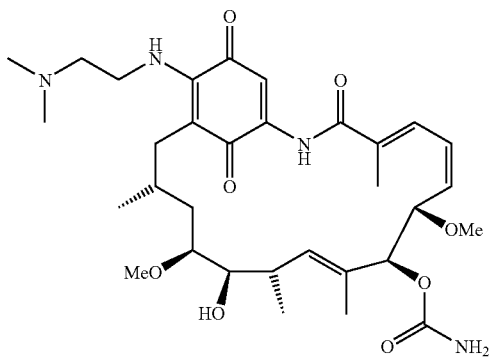 |
| IPI-504 | 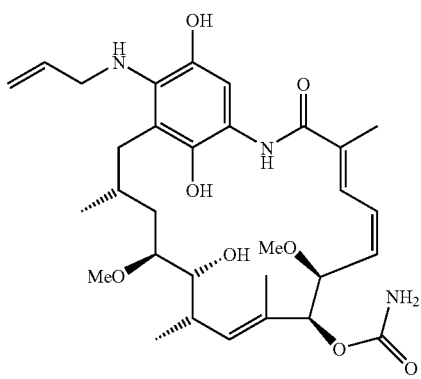 |

In another embodiment of the present disclosure, proteasome inhibitors can be used in the method of the present disclosure for inhibiting muscular-wasting diseases. Examples of suitable proteasome inhibitors include bortezomib, having the structural formula:

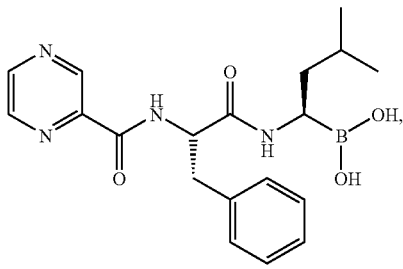

as well as its enantiomers, analogs, prodrugs, active metabolites, salts, and hydrates; and salinosporamide A, having the formula:

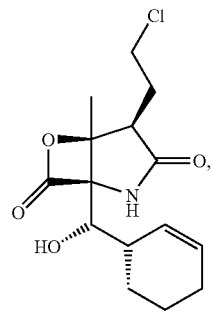

as well as its enantiomers, analogs, prodrugs, active metabolites, salts, and hydrates.

In another embodiment, the NF-κB pathway can be inhibited by rapamycin, as well as its enantiomers, analogs, prodrugs, active metabolites, salts, and hydrates. Specifically, the natural rapamycin product, having the formula:

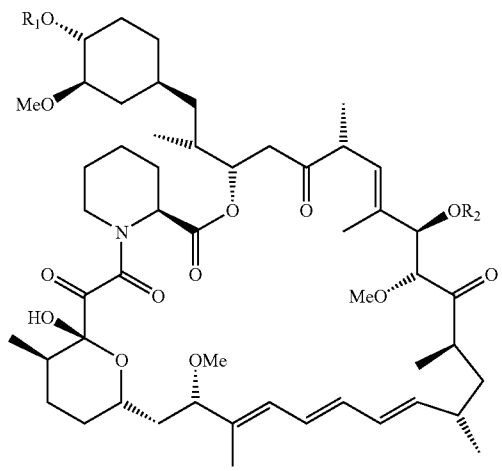

wherein $R_1$ and $R_2$ are both hydrogen, can be used as an inhibitor of the NF-κB pathway. Furthermore, analogs of rapamycin can also suitably be used as inhibitors of the NF-κB pathway. Specific suitable rapamycin analogs include, for example, those listed in Table 5.

TABLE 5

| Rapamycin Analog Inhibitors As Embodiments | |
|---|---|
| Compound name | Substituents added to Rapamycin Structural Formula |
| NSC-606698 | $R_1$ is H; and $R_2$ is COCH$_2$NMe$_2$ |
| Everolimus | $R_1$ is CH$_2$CH$_2$OH; and $R_2$ is hydrogen |
| Temsirolimus | (structure shown) $R_1$ is $R_2$ is hydrogen |
| AP-23573 | $R_1$ is PO(CH$_3$)$_2$; and $R_2$ is hydrogen |

Another inhibitor of the NF-κB pathway is zotarolimus, as described in U.S. Pat. No. 6,015,815 and PCT Application No. WO 1999/015530. Zotarolimus has the formula:

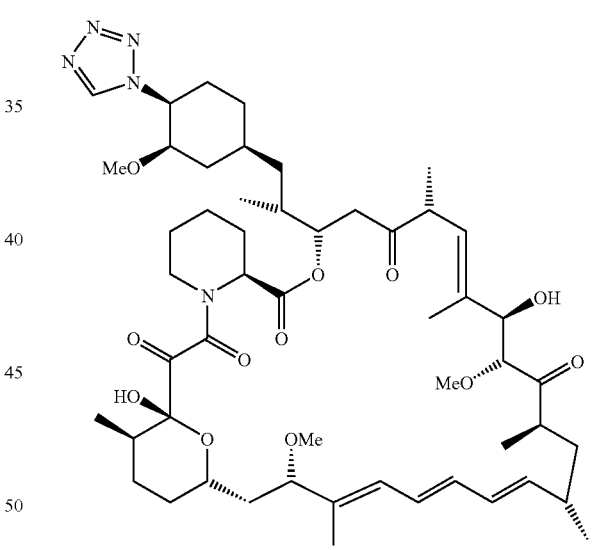

In another embodiment, curcumin, as well as its enantiomers, analogs, prodrugs, active metabolites, salts, and hydrates, can be used to inhibit the NF-κB pathway. Curcumin has the formula:

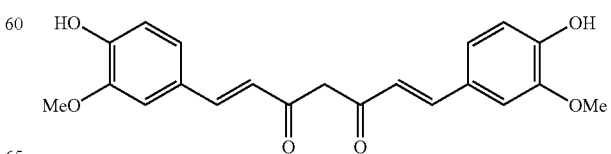

One suitable analog of curcumin is 4,4'-di-acetylcurcumin, having the formula:

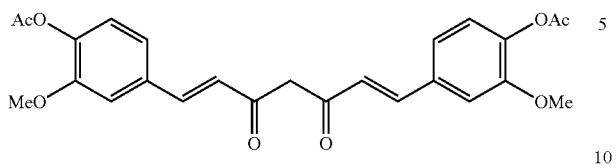

Additionally, another suitable analog of curcumin is glycosylated curcumin, having the formula:

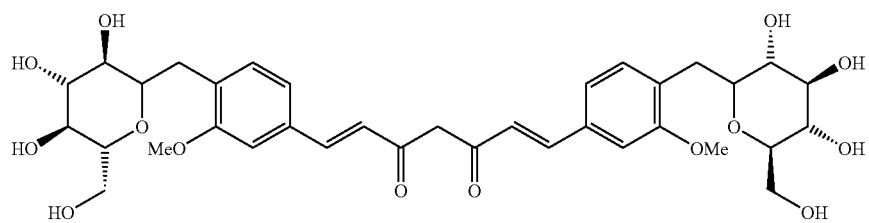

In another embodiment, thalidomide and its analogs can be used to inhibit the NF-κB pathway. Thalidomide has the formula:

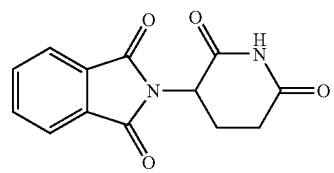 [SMILES: O=C1CCC(N2C(=O)c3ccccc3C2=O)C(=O)N1]

Analogs of thalidomide that are suitable for use in the present disclosure include CC-4047 and the (S) enantiomer, S-3APG, and lenalidomide. CC-4047 has the formula:

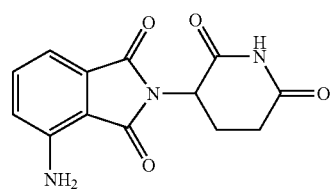 [SMILES: Nc1cccc2c1C(=O)N(C1CCC(=O)NC1=O)C2=O]

Additionally, S-3APG is described in PCT Application WO 1998/003502 and U.S. Pat. No. 5,635,517, which are both incorporated herein by reference to the extent they are consistent herewith. Furthermore, Lenalidomide has the structural formula:

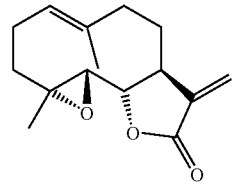

Other suitable inhibitors of NF-κB pathway include those listed in Table 6, as well as the enantiomers, analogs, prodrugs, active metabolites, salts, and hydrates thereof.

TABLE 6

Inhibitors of NF-kB as Embodiments

| Common name | Structural Formula |
|---|---|
| Parthenolide | |
| Resveratrol | 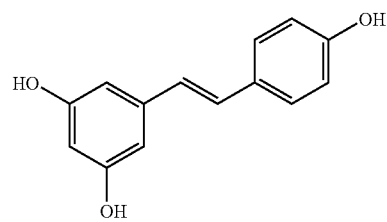 [SMILES: Oc1ccc(/C=C/c2cc(O)cc(O)c2)cc1] |
| Epoxyquinone A monomer | 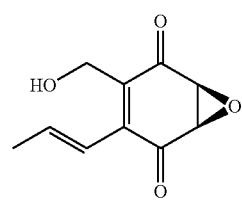 |

TABLE 6-continued

Inhibitors of NF-kB as Embodiments

| Common name | Structural Formula |
|---|---|
| Imidazoline Derivative | 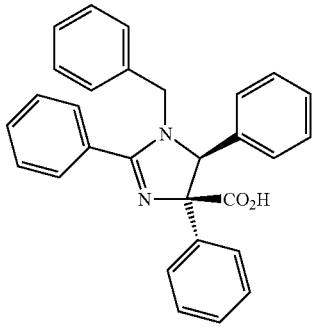 |

In yet another embodiment of the present disclosure, a combination of two or more of the above NF-κB activation inhibitors can be used to inhibit a muscular wasting disease.

Formulations

The NF-κB activation inhibitors for use in the method of the present disclosure can be formulated into pharmaceutical compositions and administered by a number of different means. Such compositions can be administered orally, parenterally, intraperitoneally, intravenously, intradermally, or transdermally.

Solid dosage forms for oral administration of the compounds may include capsules, tablets, pills, powders, and granules. In such solid dosage forms, the compounds are ordinarily combined with one or more adjuvants appropriate to the indicated route of administration. If administered in capsules or tablets, the compounds can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, or magnesium or calcium carbonate or bicarbonate. Tablets and pills can additionally be prepared with enteric coatings.

Liquid dosage forms for oral administration can include pharmaceutically acceptable emulsions, solutions, suspension, syrups, and elixirs containing inert diluents commonly used in the art, such as water. Such compositions can also comprise adjuvants, such as wetting agents, emulsifying and suspending agents, and sweetening, flavoring, and perfuming agents.

In another embodiment, the formulations can be injected into the subject for the purpose of inhibiting a muscular wasting disease. Depending upon the compound used, the compound can be administered parenterally, intraperitoneally, intratumor, or intrapleural. The term parenteral as used herein includes subcutaneous, intravenous, intramuscular, or intrasternal injection, or infusion technique.

Injectable preparations, for example sterile injectable aqueous or oleaginous suspensions, can be formulated according to the known art using suitable dispersing or wetting agents and suspending agents. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid are useful in the preparation of injectables. Dimethyl acetamide, surfactants including ionic and non-ionic detergents, and polyethylene glycols can also be used. Mixtures of solvents and wetting agents discussed herein are also useful.

In one specific injectable embodiment, the formulation is administered parentally. Formulations for parenteral administration can be in the form of aqueous or non-aqueous isotonic sterile injection solutions or suspensions. These solution and suspensions can be prepared from sterile powders or granules having one or more of the carriers of diluents mentioned for the use in the formulations for oral administration. The compounds can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

The amount of active ingredient that can be combined with the carrier materials to produce a single dosage of the NF-κB activation inhibitor will vary depending upon the subject to be treated and the particular mode of administration. In general, the NF-κB activation inhibitor can be administered to the subject in an amount of from about 0.001 mg/kg to about 100.0 mg/kg body weight. More suitably, the NF-κB activation inhibitor is administered to the subject in an amount of from about 0.01 mg/kg to about 10.0 mg/kg, even more suitably, from about 0.1 mg/kg to about 1.0 mg/kg, even more suitably, from about 0.1 mg/kg to about 0.5 mg/kg, and even more suitably, about 0.3 mg/kg. Typically, the NF-κB activation inhibitor is administered to the subject once per day.

EXAMPLES

The following examples are simply intended to further illustrate and explain the present disclosure. The disclosure, therefore, should not be limited to any of the details in these examples.

Example 1

In this Example, the DNA binding activity of NF-κB in the skeletal muscles of both healthy control mice and mdx null mice (mdx−/−) was evaluated using electrophoretic mobility shift assay (EMSA).

The diaphragm muscles from six mdx−/− mice, at an age of three to five weeks old, were removed and nuclear extracts were prepared for use in an EMSA to measure the DNA binding activity of NF-κB.

The diaphragm muscles of control mice (C57/BL10) were also removed and nuclear extracts were prepared for use in an EMSA.

The results of the EMSA for both the mdx−/− mice and control mice were compared and are shown in FIG. 1 below. As shown in FIG. 1, the NF-κB activity of the diaphragm muscles was substantially higher in the mdx−/− mice as compared to the control mice.

Figure 2:
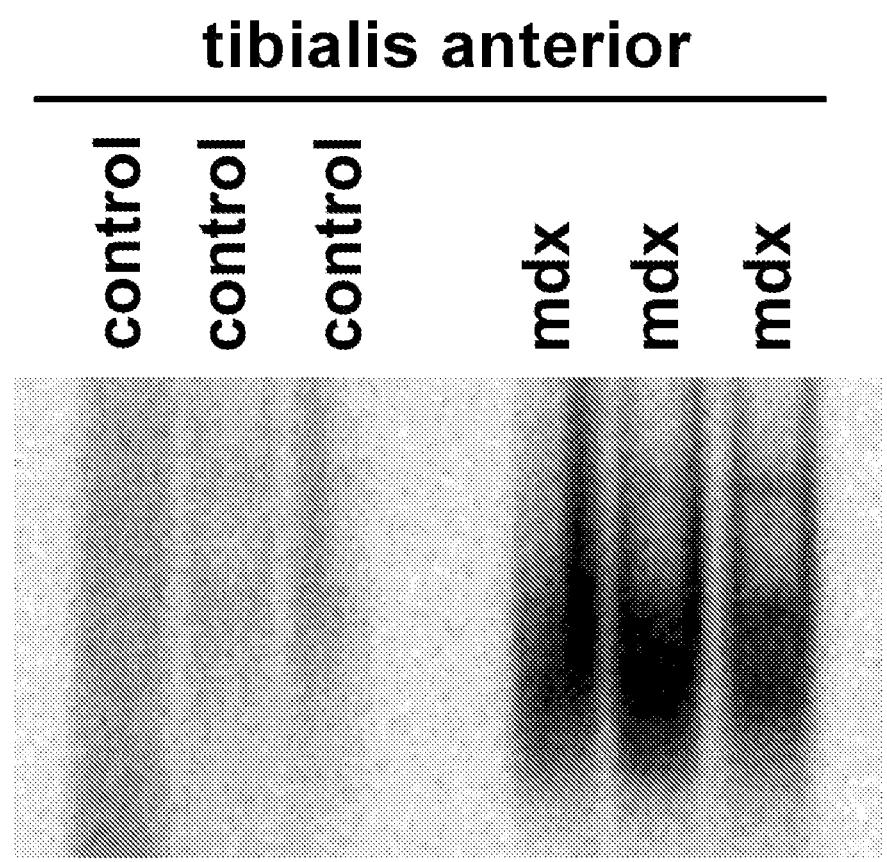
FIG. 2 depicts the EMSA analysis of Tibialis anterior muscles harvested from control and mdx-/- mice as conducted in Example 1.

EMSA analysis also revealed that similar reproducible increases in NF-κB activity were observed in mdx−/− tibialis anterior muscles tested using the same method as the diaphragm muscles above. The results of the EMSA analysis are shown in FIG. 2.

Example 2

In this Example, mdx−/− mice were crossed with p65 heterozygous mice. The litter was then evaluated to determine if the activation of NF-κB in the mdx−/− mice found in Example 1 above contributes to muscular dystrophy.

Mdx−/− mice were crossed with p65 heterozygous mice (p65+/−), and at five weeks old, six litter mates were sacrificed and the tibialis anterior muscles of the litter mates were isolated surgically, frozen for ten seconds at a temperature of about −120° C., and subsequently sectioned for histological analysis. The sections of tibialis anterior muscles were about 10 μm in size.

The sectioned muscles of healthy control mice, mdx−/− mice, and mice heterozygous for NF-κB (P65+/−) were analyzed using H&E staining. The results are shown in FIG. 3.

Figure 3:
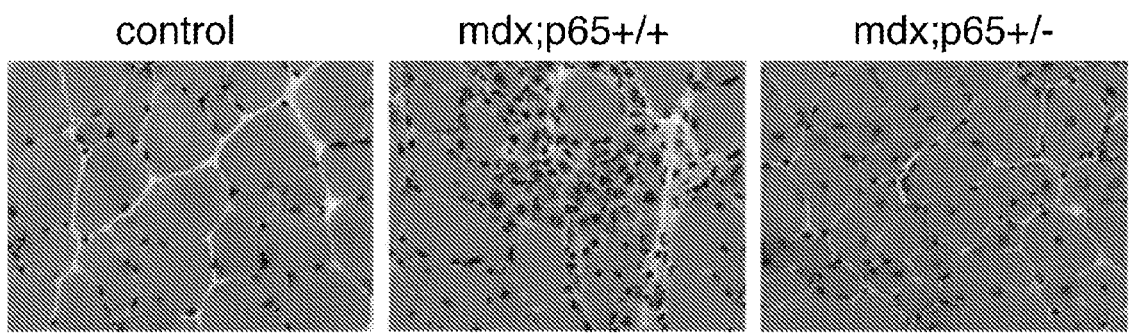
FIG. 3 depicts H&E staining of tibialis anterior muscle cells of control mice, mdx-/- mice, and mice heterozygous for NF-κB (p65+/-) as conducted in Example 2.

As shown in FIG. 3, the litter mice that were mdx heterozygous for NF-κB (p65+/−) had a significant reduction of disease phenotype as compared to the mdx−/− mice alone, as characterized by reduced immune cell infiltrate and fiber necrosis.

The sectioned muscles were additionally analyzed for regenerative ability using immunohistochemical staining with the regenerative marker embryonic myosin (MyHC). The results of the MyHC immunohistochemical staining are shown in FIG. 4.

Figure 4:
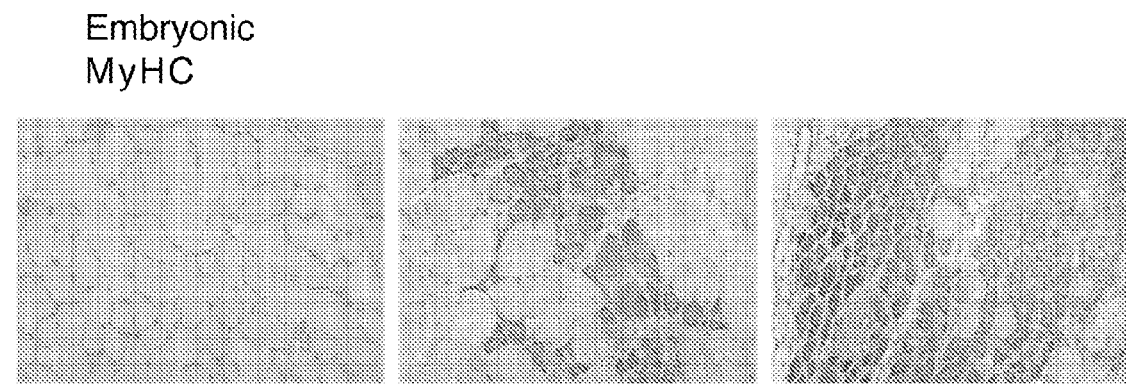
FIG. 4 depicts regenerative marker embryonic myosin (MyHC) immunohistochemical staining of tibialis anterior muscle cells of control mice, mdx-/- mice, and mice heterozygous for NF-κB (p65+/-) as conduced in Example 2.

As shown in FIG. 4, the litter mice that were mdx heterozygous for NF-κB (p65+/−) had an enhanced regenerative capability as compared to the mdx−/− mice alone.

Example 3

In this Example, three week old male mdx−/− mice were treated with various peptides comprising NEMO binding domains. The diaphragm muscles of the mice were then evaluated to determine the ability of the peptides to treat muscle wasting in the mdx mice.

Three week old mdx−/− mice were treated by intraperitoneal injections with 200 μg of either a wild type peptide (SEQ ID NO 19) comprising a NEMO binding domain or a mutant peptide (SEQ ID NO 20). The mice were injected every three days for a total trial period of 27 days. After 27 days, the mice were sacrificed and the diaphragm muscles were removed.

The diaphragm muscles were placed in a chamber filled with Ringer solution and perfused continuously with an $O_2/CO_2$ mixture. The muscles were then attached using a steel hook to a force transducer and subsequently stimulated at varying frequencies. At each frequency, forces were allowed to reach a steady state before the data was recorded.

Figure 5:
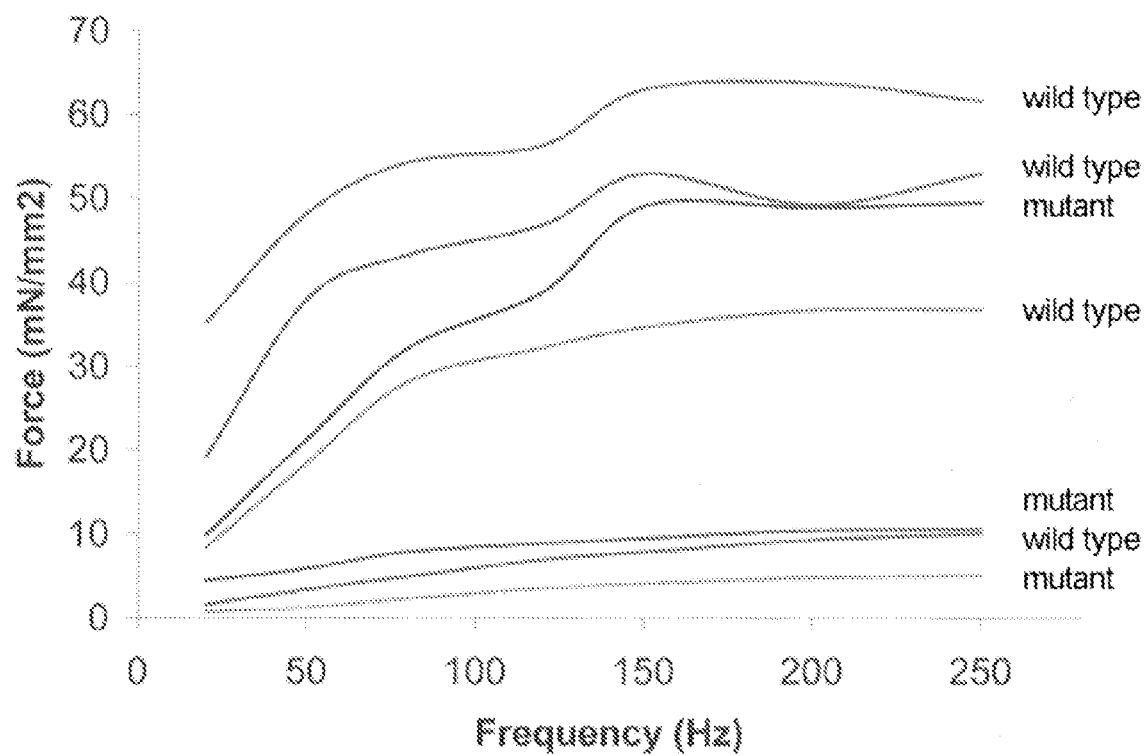
FIG. 5 is a graph illustrating the amount of force stimulating the diaphragm muscles of mice over various frequencies as tested in Example 3.

Results of the force measurements at the various frequencies are shown in FIG. 5. As shown in FIG. 5, the diaphragm muscles from the mdx−/− mice treated with wild type peptide comprising a NEMO binding domain had generally higher tentanic contractions compared to mice treated with the mutant peptide. Specifically, force output was higher in three of the four wild type peptide treated mice compared to only one of the three mutant peptide treated mice. Consequently, this data suggests that the wild type peptide comprising the NEMO binding domain is capable of treating contractile dysfunction in the mdx−/− mice model of Duchenne muscular dystrophy.

Example 4

In this Example, the requirement of the NF-κB signaling pathway in skeletal muscle fibers was analyzed. Specifically, mdx−/−;IKKβ$^{FL}$ mice were crossed with Cre-transgenic knock-in mice. The litter was then evaluated to determine if the blocking of the NF-κB signaling pathway, specifically reducing the level of IKKβ in skeletal muscle fibers, could increase skeletal muscle regeneration.

Mdx−/−;IKKβ$^{FL}$ mice were crossed with Cre-transgenic knock-in mice under the regulation of the myosin light chain 1f promoter (MLC-Cre), whose expression has been shown to be highly restricted to skeletal muscles. Surprisingly, genotyping analysis (i.e., PCR analysis) from over 100 progeny showed that MLC-Cre mice were not obtained in the expected Mendelian ratios and greater than 98% of the viable mdx−/−; IKKβ$^{FL}$;MLC-Cre litters were females. This suggested that there was a sex bias in the segregation of these alleles. Since expression of MLC-1f occurs early in skeletal muscle development, it is possible that the requirement of IKKβ during embryonic development might be differently regulated in a sex specific manner in a dystrophic background.

Figure 6:
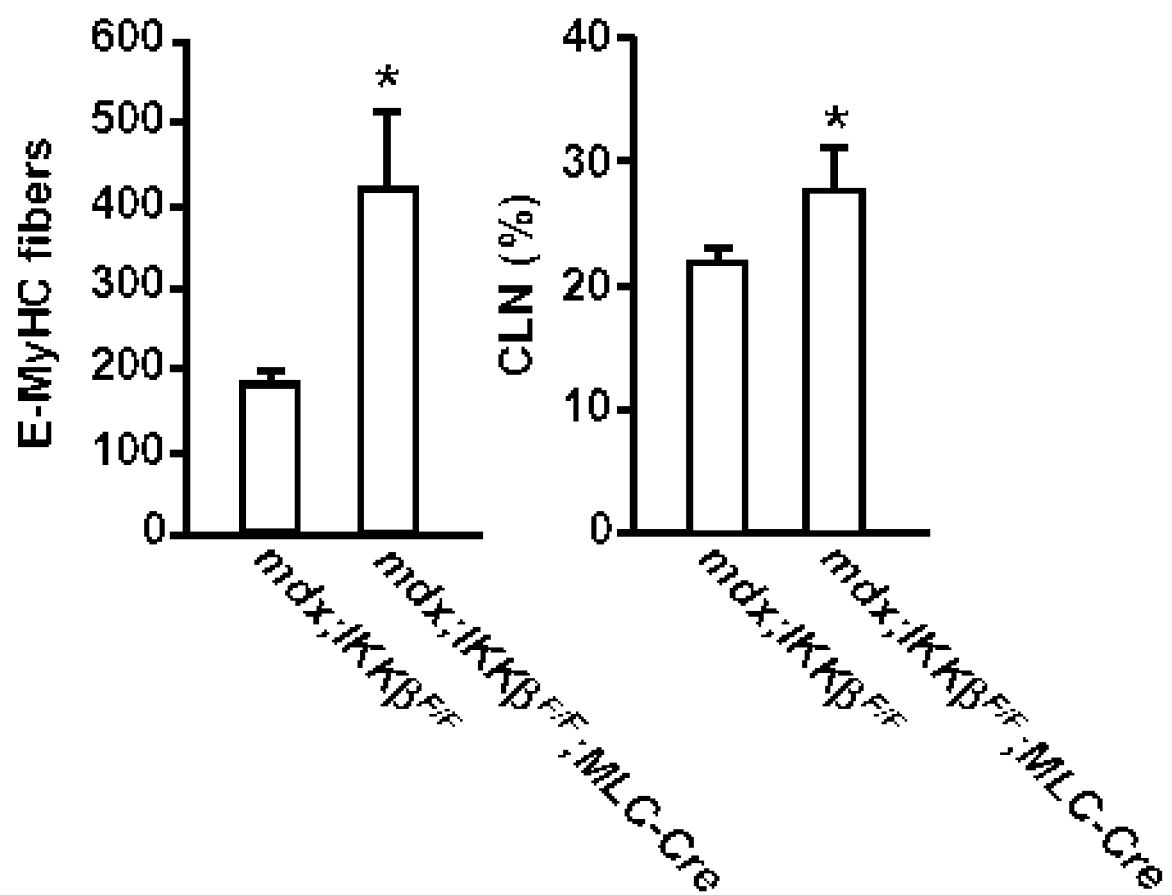
FIG. 6 is a graph illustrating the results of E-MyHC immunohistochemical staining and scoring of centronucleated fibers in mice as tested in Example 4.

Based on these considerations, mdx−/−/IKKβ$^{FL}$;MLC-Cre female mice at four weeks of age were utilized for the analyses described more fully below and then the results of the analyses were compared to the results of age matched mdx−/−;IKKβ$^{FL}$ female control mice. The mice were sacrificed and the quadricep muscles were isolated surgically, frozen for ten seconds at a temperature of about −120° C., and subsequently sectioned for histological analysis. The sectioned muscles were additionally analyzed for regenerative ability using immunohistochemical staining with the regenerative marker embryonic myosin (MyHC) and quantitatively confirmed by E-MyHC staining and by scoring for centronucleated fibers. The results of the E-MyHC immunohistochemical staining and scoring analyses are shown in FIG. 6. As shown in FIG. 6, there are increased levels of myosin heavy chain in the mdx−/−/IKKβ$^{FL}$;MLC-Cre mice as compared to the mdx−/−;IKKβ$^{FL}$ control mice, indicating that the mdx−/−/IKKβ$^{FL}$;MLC-Cre mice have larger and healthier muscle fibers.

Figure 7:
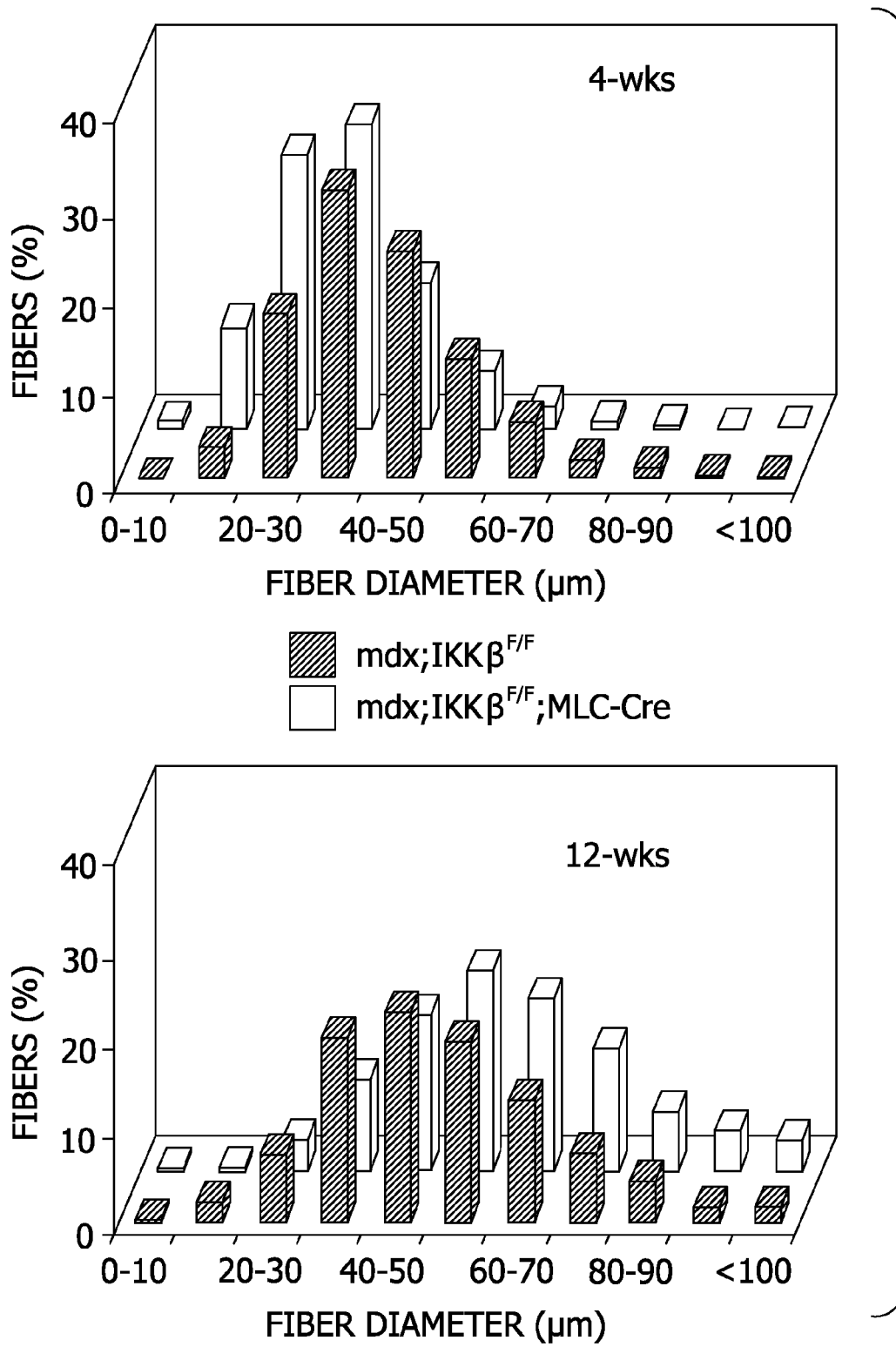
FIG. 7 is a graph illustrating the results of fiber diameter measurements as tested in Example 4.

Furthermore, morphometric measurements revealed that at 4 weeks, regenerative fibers in mdx−/−;IKKβ$^{FL}$; MLC-Cre mice were smaller as compared to mdx/IKKβ$^{FL}$ mice. However, when fiber diameter measurements were repeated at 12 weeks of age, fibers in mdx−/−;IKKβ$^{FL}$; MLC-Cre muscles were found to be significantly larger (see FIG. 7), suggesting that the higher regeneration capacity in mdx−/−;IKKβ$^{FL}$; MLC-Cre mice eventually culminated in more mature fiber formation. Taken together, these results support a pathway of IKKβ-mediated NF-κB regulation in skeletal muscle that functions to inhibit regeneration in muscular dystrophy.

The present disclosure is not limited to the above embodiments and can be variously modified. The above description of preferred embodiments is intended only to acquaint others skilled in the art with the disclosure, its principles and its practical application so that others skilled in the art may adapt and apply the disclosure in its numerous forms, as may be best suited to the requirements of a particular use.

With reference to the use of the word(s) "comprise" or "comprises" or "comprising" in this entire specification (including the claims below), it is noted that unless the context requires otherwise, those words are used on the basis and clear understanding that they are to be interpreted inclusively, rather than exclusively, and that it is intended each of those words to be so interpreted in construing this entire specification.

What is claimed is:

1. A method of treating Duchenne muscular dystrophy in a subject in need thereof, the method comprising administering to the subject an NF-κB activation inhibitor comprising amino acid sequence of SEQ ID NO:19.

2. The method as set forth in claim 1 wherein the NF-κB activation inhibitor is amino acid sequence of SEQ ID NO: 19.

3. The method as set forth in claim 1 wherein the NF-κB activation inhibitor is administered to the subject in an amount of from about 0.001 mg/kg to about 100.0 mg/kg.

* * * * *